(12) United States Patent
Sepetka et al.

(10) Patent No.: US 6,663,650 B2
(45) Date of Patent: Dec. 16, 2003

(54) SYSTEMS, METHODS AND DEVICES FOR REMOVING OBSTRUCTIONS FROM A BLOOD VESSEL

(75) Inventors: Ivan Sepetka, Los Altos, CA (US); Martin Dieck, Cupertino, CA (US); Son Gia, San Jose, CA (US)

(73) Assignee: Concentric Medical, Inc., Mountain View, CA (US)

( * ) Notice: Subject to any disclaimer, the term of this patent is extended or adjusted under 35 U.S.C. 154(b) by 0 days.

(21) Appl. No.: 09/756,476

(22) Filed: Jan. 8, 2001

(65) Prior Publication Data
US 2002/0002383 A1 Jan. 3, 2002

Related U.S. Application Data

(63) Continuation-in-part of application No. 09/605,143, filed on Jun. 29, 2000.

(51) Int. Cl.[7] .............................................. A61M 29/00
(52) U.S. Cl. ...................................................... 606/200
(58) Field of Search ................................ 606/159, 191, 606/192, 194, 198, 200

(56) References Cited

U.S. PATENT DOCUMENTS

| | | | | |
|---|---|---|---|---|
| 5,908,435 A | * | 6/1999 | Samuels | 606/200 |
| 5,972,019 A | * | 10/1999 | Engelson et al. | 606/200 |
| 6,066,158 A | * | 5/2000 | Engelson et al. | 606/200 |

* cited by examiner

*Primary Examiner*—Danny Worrell
*Assistant Examiner*—Shaun R Hurley
(74) *Attorney, Agent, or Firm*—Jens E. Hoekendijk; Hoekendijk & Lynch, LLP

(57) ABSTRACT

A system for removing an obstruction from a blood vessel includes an obstruction engaging element and an expandable capture element. The capture element preferably has a flexible cover and an expandable support structure. The engaging element engages the obstruction and moves the obstruction into the capture element. The capture element protects the obstruction when the obstruction is moved into the catheter.

29 Claims, 20 Drawing Sheets

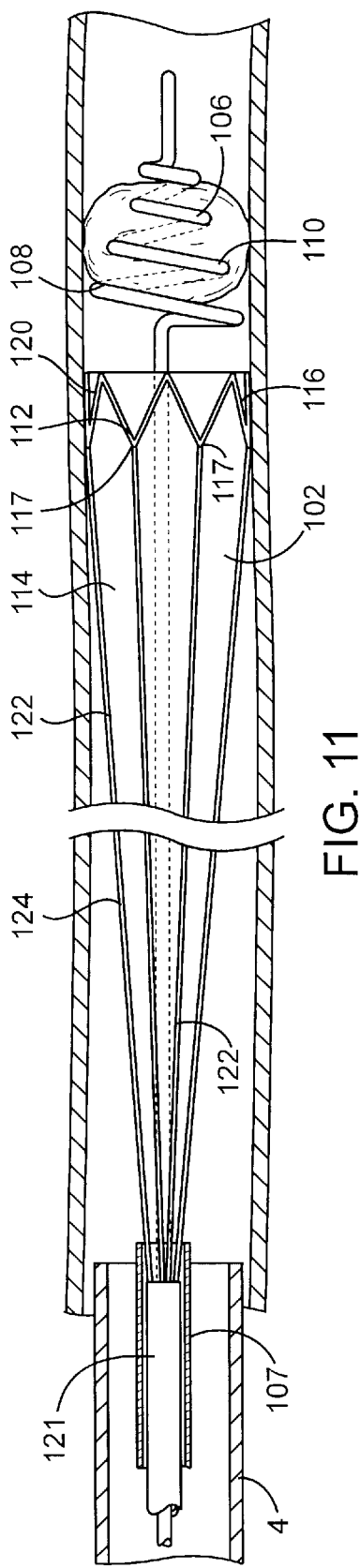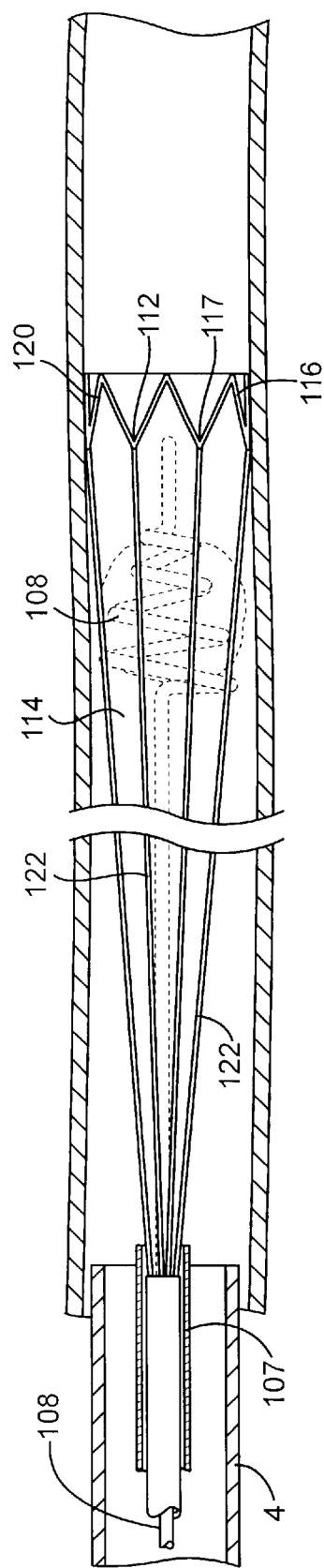

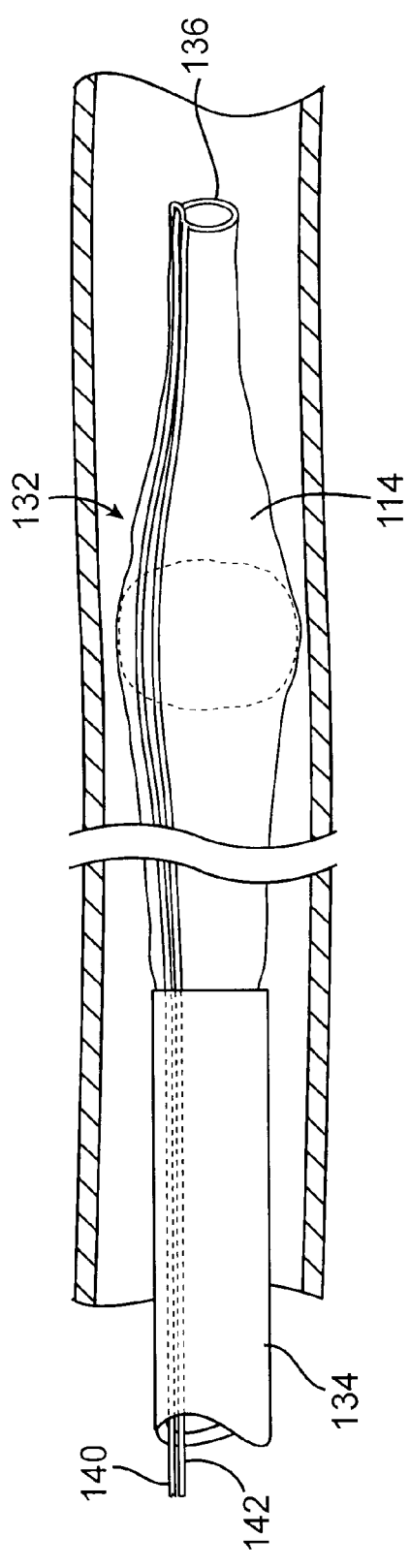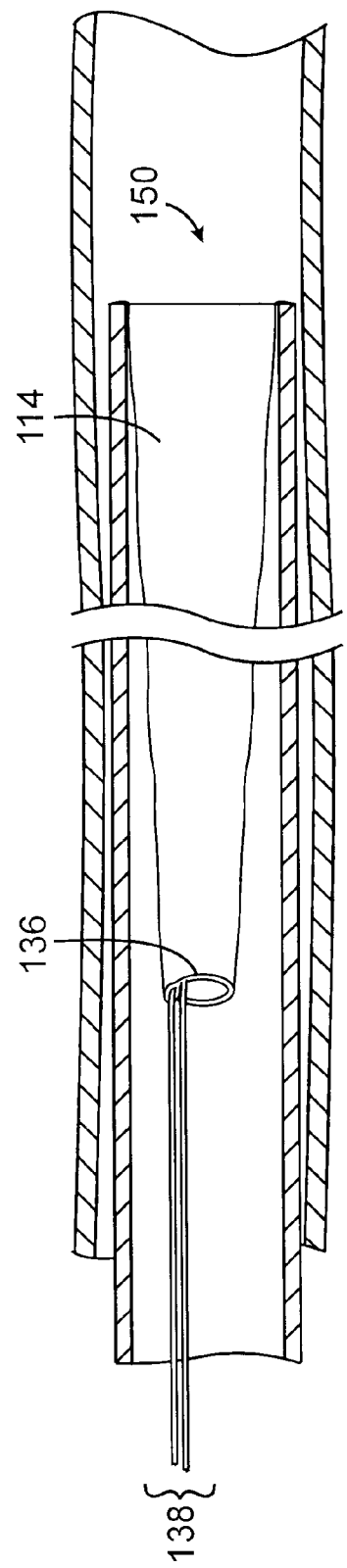
FIG. 18
FIG. 19

SYSTEMS, METHODS AND DEVICES FOR REMOVING OBSTRUCTIONS FROM A BLOOD VESSEL

CROSS-REFERENCE TO RELATED APPLICATIONS

The present application is a continuation-in-part of application Ser. No. 09/605,143, filed Jun. 29, 2000, entitled, "Methods and Devices for Removing an Obstruction From a Blood Vessel," by inventors Sepetka, et al., the full disclosure of which is incorporated herein by reference.

BACKGROUND OF THE INVENTION

The present invention is directed to methods and devices for removing obstructions from blood vessels. The device may be used to retrieve and remove clots and other biological obstructions. The device may also be used to retrieve embolic coils and the like which have been misplaced or have migrated to an undesirable location.

One such obstruction removal device is disclosed in U.S. Pat. No. 5,895,398 which is hereby incorporated by reference. The device has an expandable engaging member which is introduced into the blood vessel to engage the obstruction for removal.

The present invention is also directed to devices, systems and methods which use an expandable capture element when removing obstructions from a blood vessel. One such system for removing obstructions in a blood vessel is described in U.S. Pat. No. 5,102,415 to Guenther et al. The system described in U.S. Pat. No. 5,102,415 has a balloon catheter and a catheter having an expandable tip which receives the obstruction. The balloon catheter is passed through the obstruction while the balloon is deflated. The balloon is then inflated and the tip of the catheter is expanded. The balloon is then moved proximally so that the obstruction is pulled into the expanded tip of the catheter. A problem with the system of U.S. Pat. No. 5,102,415 is that the interaction between the balloon catheter and the leading edge of the catheter may tend to shear off portions of the obstruction. This can cause obvious problems when working in sensitive vascular areas.

The present invention is directed to additional devices and methods for removing obstructions in a blood vessel.

SUMMARY OF THE INVENTION

In accordance with the present invention, device and methods for removing obstructions are provided. In a first aspect of the invention, an obstruction removal device is provided which has an obstruction engaging element extending from an insertion element. The engaging element is movable from a collapse position to an expanded position. The engaging element forms coils having varying diameter wherein the coils at a distal portion are larger than coils at an intermediate portion. The distal portion forms a relatively closed structure which prevents the obstruction, or any part thereof, from migrating downstream. The distal portion is expanded distal to the obstruction while the proximal portion engages and holds the obstruction.

In another aspect of the present invention, another obstruction removal device is provided which has at least one closed loop and preferably two closed loops. The closed loop provides an advantage when advanced through a catheter or sheath in that the closed loop produces opposing radial forces on the catheter or sheath through which the loop is advanced. In this manner, the obstruction removal device can be advanced more easily through the catheter or sheath to prevent binding or kinking of the device during advancement. In a preferred embodiment, the obstruction removal device has two loops of varying diameter with the distal loop having a larger diameter. Each of the loops lie in a plane with the planes of the two loops preferably being perpendicular to one another.

In another aspect of the invention, another obstruction removal device is provided which has wound sections formed by one or more filaments which are separated by sections substantially free of the filaments. The intermittent wound sections provide discrete portions where the obstruction can be engaged. In an embodiment, the wound sections can slide on the core element to provide flexibility when advancing the obstruction removal device. The wound sections and sections free of filament are preferably about 1–5 mm long. The obstruction removal device preferably has at least three wound sections and more preferably at least five wound sections.

In still another aspect of the invention, another obstruction removal device is provided which has alternating large and small diameter portions. In a preferred embodiment, the obstruction removal device has at least four large diameter sections and three smaller diameter portions. The alternating large and small diameter portions may help to engage certain types of obstructions and can also help to prevent parts of the obstruction from breaking off and migrating downstream.

Any of the obstruction removal devices described herein may also be used with a source of power coupled to the obstruction removal device for use as described below. The source of power may simply produce a positive or negative charge or may be an RF energy source. The source of power may be used to help the obstruction removal device penetrate and engage the obstruction and may also be used to adhere the obstruction to the obstruction removal device as will be described. In a preferred embodiment, a negative charge is provided when advancing the obstruction removal device into the obstruction and a positive charge, or RF energy, is supplied to adhere the device to the obstruction.

The devices of the present invention may be manufactured in any suitable manner. In another aspect of the present invention, the obstruction removal device has a core element surrounded by a sheath. A strand, preferably about four strands, are positioned between the core element and the tube. The strand and the tube prevent any part of the obstruction removal device from breaking free should the core element fail. The strand and tube will hold the obstruction removal device together even if the core element breaks. The sheath is preferably flexible so that the sheath can undergo much larger deflections than the core element.

The obstruction removal devices of the present invention may also be advanced through a guide catheter having a flow restricting element which is preferably a balloon but may be any other suitable structure. The flow restricting element is expanded to reduce blood flow through the obstructed vessel to minimize the likelihood that the obstruction will migrate downstream.

In another aspect of the invention, a system is provided which has an expandable capture element and an obstruction engaging device which together work to remove an obstruction from a blood vessel. The capture element is advanced through the patient in a collapsed position and is expanded when at the desired location. The obstruction engaging device preferably has one or more filaments which provide a relatively flexible interaction between the engaging device and the capture element. This provides advantages over the use of a balloon catheter as described in greater detail below. The obstruction engaging device preferably has 1–4 filaments and more preferably 1–2 filaments. Of course, the obstruction engaging device may have more filaments without departing from various aspects of the invention and, in fact, the device may form a filter which further helps to prevent portions of the obstruction from being carried downstream.

The capture element is preferably naturally biased toward the expanded position although the capture element may also be manually actuated as described below.

The capture element has a support structure with a flexible cover attached thereto. The support structure preferably has a closed loop which opens the distal end of the cover. The loop is preferably integrally formed and has a number of integrally formed hinges which deflect when the loop is expanded and collapsed. The hinges are preferably V-shaped although other shapes may be used. A plurality of struts extend proximally from the loop.

The capture element may also be expanded by the user so that the user may select the appropriate time for expansion of the capture element. In this manner, the user may advance the capture element to a suitable location for expansion. The user may also collapse the capture element before withdrawing the capture element into a catheter. The capture element has an actuator for opening and closing the capture element. The actuator may have a control arm and a stable arm although any suitable actuator may be used. The control arm is manipulated to expand and contract a loop at the distal end of the capture element. Alternatively, the actuator may be a tube which cinches the loop closed. In a specific embodiment, the capture element may also evert when moving to the expanded position.

The device of the present invention may be used in various different locations and for various different purposes. In one embodiment, the device may be used in connection with a guide catheter. When used with the guide catheter, the device may be expanded to slow or even stop blood flow when performing other procedures downstream of the guide catheter such as removing a clot or placing a stent.

Alternatively, the device may be passed through a conventional guide catheter so that the device may be introduced further into the vasculature. In this system, the capture element passes through the guide catheter. The obstruction engaging device is then used to engage the obstruction and move the obstruction into the capture element.

These and other advantages of the invention will become apparent from the following description, drawings and claims.

BRIEF DESCRIPTION OF THE DRAWINGS

FIG. 11 shows a capture element in an expanded position with an obstruction engaging element engaging an obstruction.

FIG. 12 shows the obstruction moved into the capture element with the obstruction engaging element.

FIG. 18 shows the capture element collapsed around the obstruction prior to withdrawal.

FIG. 19 shows the capture element contained within the catheter in an inverted position when collapsed.

DESCRIPTION OF THE PREFERRED EMBODIMENTS

Figure 1:
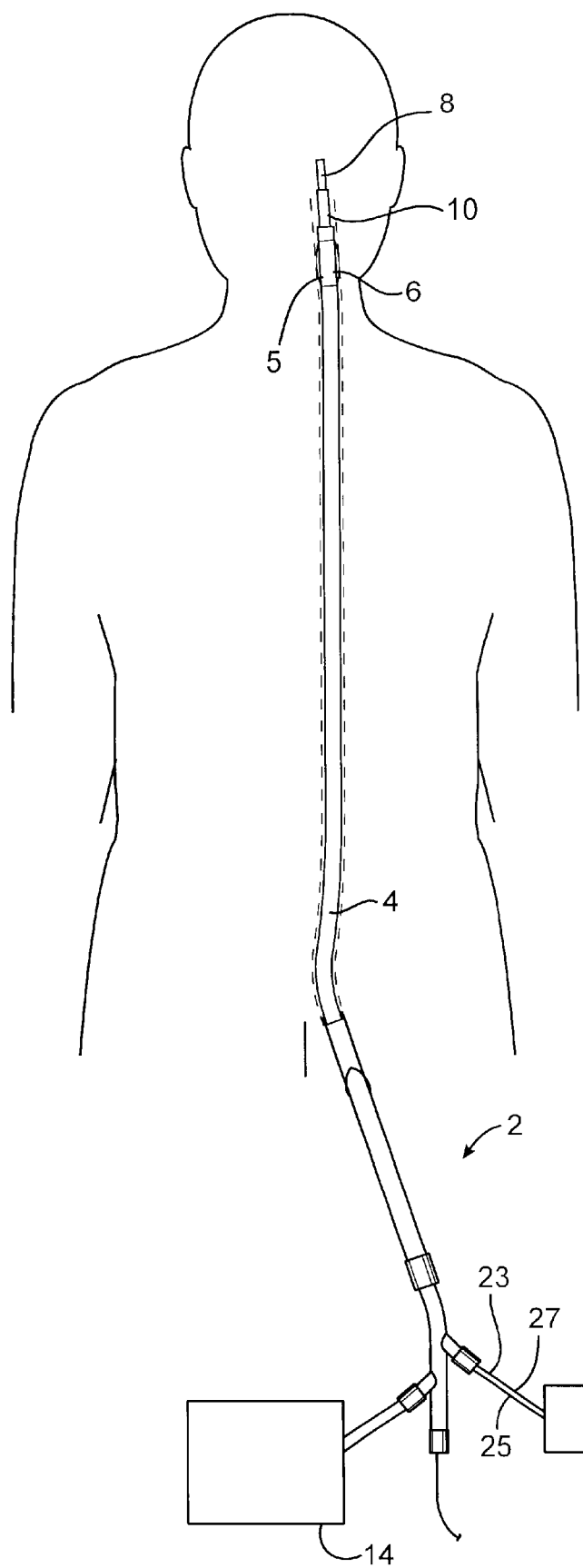
FIG. 1 shows a system for removing an obstruction.
Figure 2:
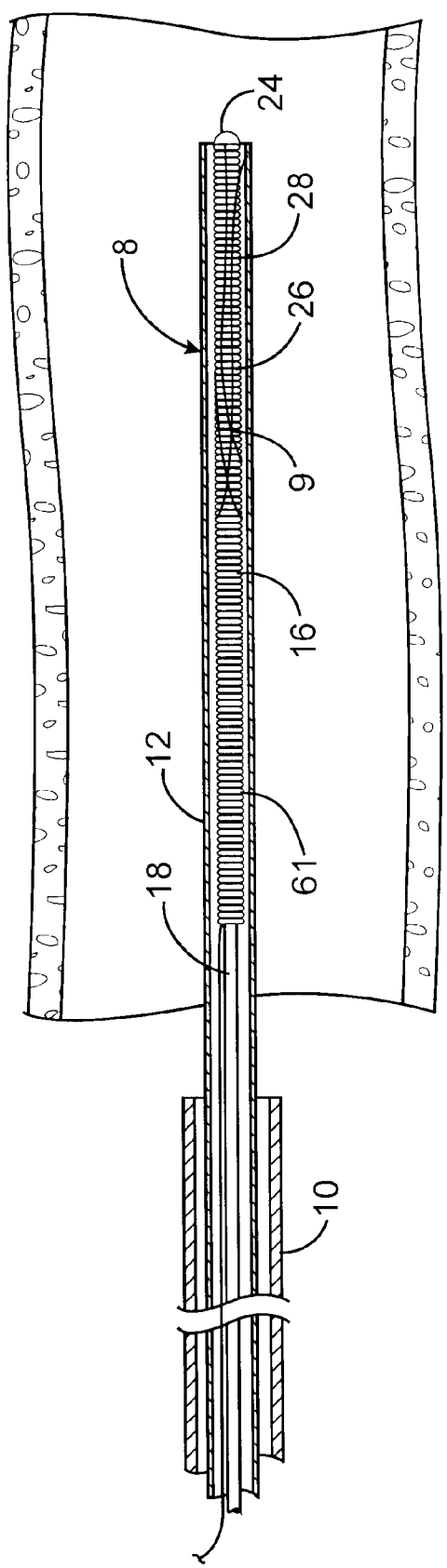
FIG. 2 shows the obstruction removal device in a collapsed condition.

Referring now to FIGS. 1–4, a system 2 for removing an obstruction is shown. A guide catheter 4 is advanced to a location proximal to an obstruction. When accessing the cerebral vasculature, for example, the guide catheter 4 is often positioned in the carotid or vertebral artery. Of course, the guide catheter 4 may not be necessary or may be positioned in any other suitable location depending upon the location of the obstruction. The guide catheter 4 preferably has a flow restricting element 6 which restricts or even stops blood flow through the vessel as described below. The flow restricting element 6 is preferably a balloon 5 coupled to a source of inflation fluid 7 which is used to inflate the balloon 5.

An obstruction removing device 8 is advanced through the guide catheter 4 to the obstruction. A microcatheter 10 may also be positioned within the guide catheter 4 to deliver the obstruction removing device 8 further into the vasculature. The obstruction removing device may be advanced by itself through the microcatheter 10 or may be contained within a sheath 12 which is advanced through the microcatheter 10. A source power 14 may also be coupled to the obstruction removal device 8 for use in the manner explained below. The power source 14 may simply produce a positive or negative charge or may be an RF or other suitable power source.

Figure 3:
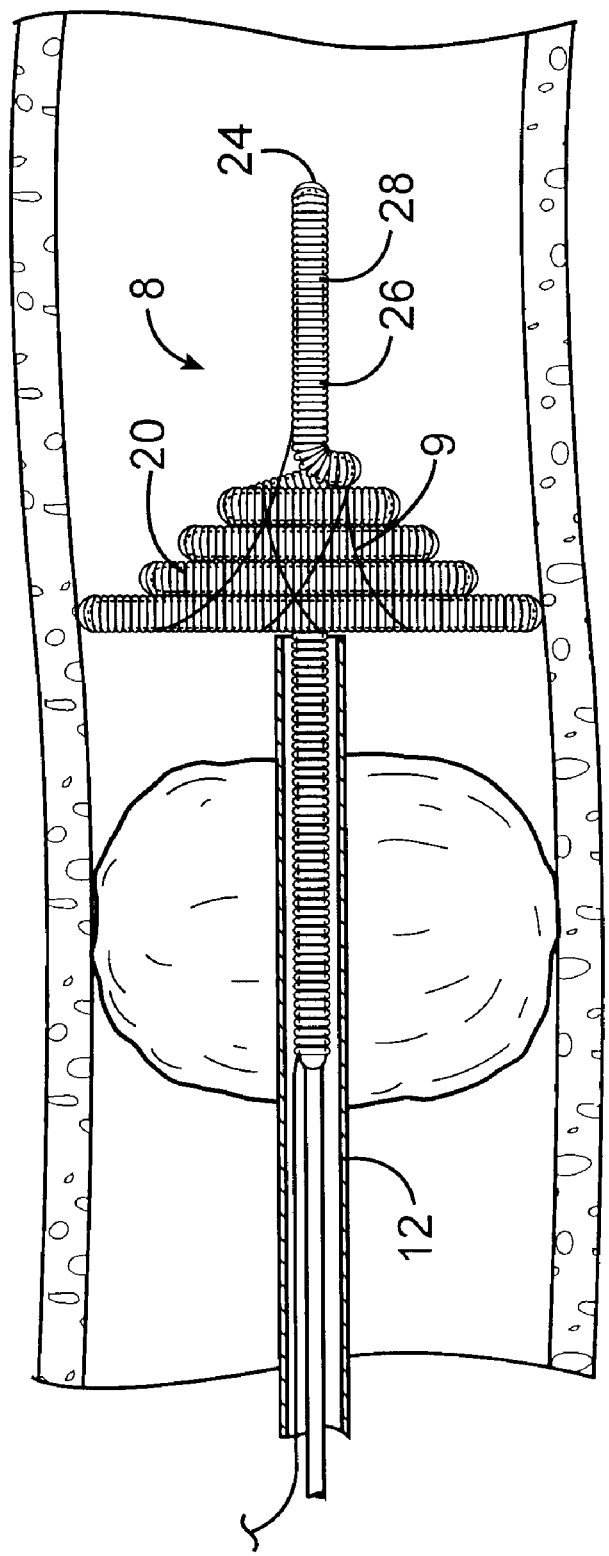
FIG. 3 shows the obstruction removal device with a distal portion of the obstruction removal device expanded.
Figure 4:
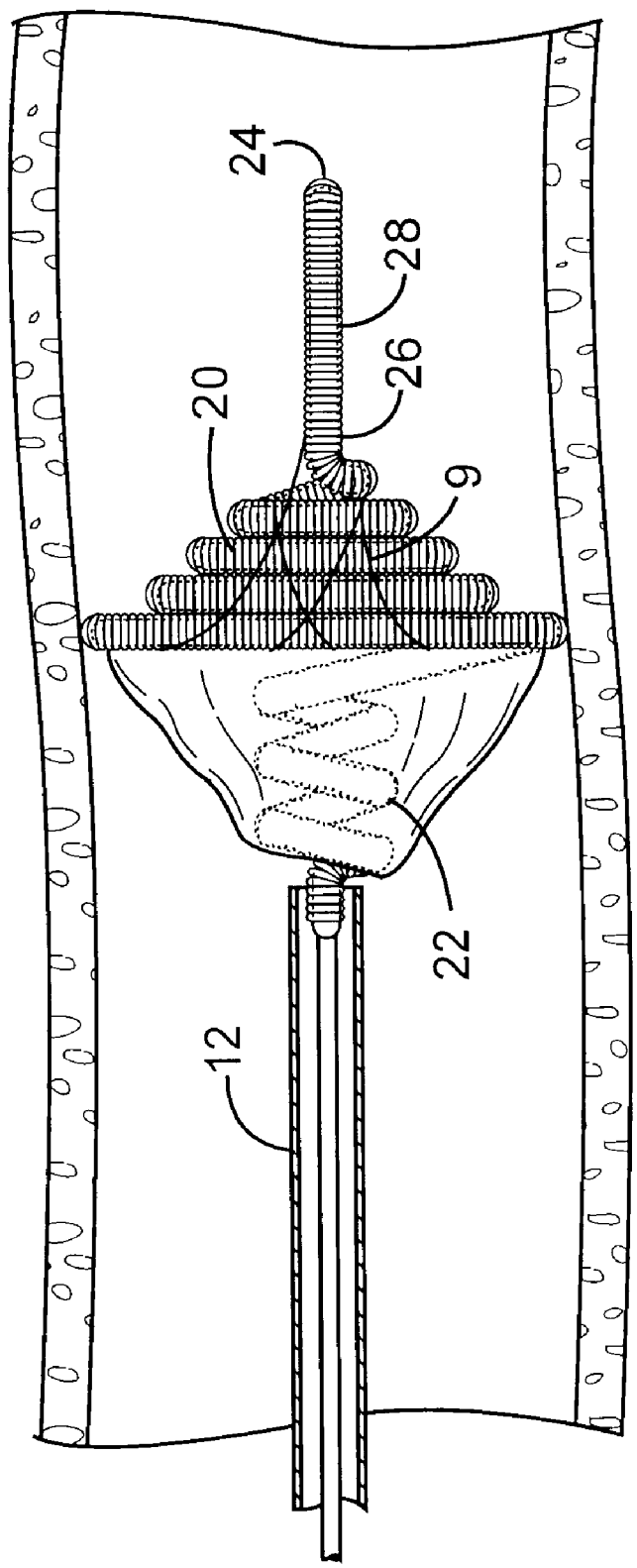
FIG. 4 shows the obstruction removal device with a proximal portion expanded to engage an obstruction.

The obstruction removing device 8 has an engaging element 16 extending from an insertion element 18. The engaging element 16 is movable from a collapsed position (FIG. 2) to an expanded position (FIGS. 3 and 4). When the engaging element 16 is contained within the sheath 12 or microcatheter 10, the engaging element 16 is in a relatively straight configuration. The engaging element 16 has a distal portion 20, which forms a relatively closed structure, which can catch or trap the obstruction, or any part thereof, to prevent migration of the obstruction or part thereof. The engaging element 16 has a proximal portion 22 which is formed with smaller coils than the distal portion 20. The proximal portion 22 engages the obstruction as described below.

The engaging element 16 preferably has a number of markers 23, 25, 27 which provide an indication as to how much of the engaging element 16 extends from the sheath 12 or microcatheter 10. For example, markers 23, 25, 27 may indicate when the engaging element 16 is ½, ¾ or fully exposed. In this manner, the user may quickly advance the engaging element engaging element 16 through the sheath 12 or microcatheter 10 without inadvertently exposing and advancing the engaging element 16 out of the sheath 12 or microcatheter. The markers 23, 25, 27 can also be used to provide a controlled diameter of the engaging element 16 since the diameter of the engaging element 16 is known for the various positions corresponding to the markers 23, 25, 27. The markers 23, 25, 27 may also be used to size the vessel in which the engaging element 16 is positioned by observing when the engaging element 16 engages the vessel walls and determining the size of the engaging element 16 using the markers 23, 25, 27.

The insertion element 18 is preferably made of a superelastic material or stainless steel having a diameter of 0.004 to 0.038 inch and preferably about 0.010 inch. Although the insertion element 18 is preferably a solid, elongate element, the insertion element 18 may take any other suitable structure such as a hollow tube. The engaging element 16 is preferably made of a superelastic material, such as nitinol, and has a diameter of 0.005–0.018 inch, more preferably 0.005–0.010 inch and most preferably about 0.008 inch. The engaging element 16 has a rounded, atraumatic tip 24 to prevent damage to the vessel and facilitate advancement through the vessel, microcatheter 10 and/or sheath 12. A radiopaque wire 26, such as platinum ribbon 28 having a width of 0.004 inch and a thickness of 0.002 inch, is preferably wrapped around the engaging element 16 to improve radiopacity.

The device 8 is preferably self-expanding but may also be expanded with an actuator 29. The actuator 29 is preferably a thin filament which is tensioned to move the device 8 to the expanded position. An advantage of the invention is that the filament 29 extends through the same lumen as the device 8 thereby minimizing the overall size of the device. It is understood that throughout discussion of the devices and methods herein that any of the devices may be expanded using the actuator 29 rather than being self-expanding without departing from the scope of various aspects of the invention.

The device 8 may also include a cover 9 which extends between adjacent coils. The cover 9 may be a number of individual strands 11 which extend between the coils or may be an elastic membrane which covers the coils. The strands 11 are preferably elastic to stretch when the device 8 is expanded.

Use of the obstruction removing device 8 is now described. The guide catheter 4 is introduced into the patient and delivered proximal to the target vessel such as to the carotid or vertebral artery. The microcatheter 10 is then advanced through the guide catheter 4 further into the vasculature to a position proximal to, within or distal to the obstruction. The obstruction removal device 8 is then advanced through the microcatheter 10 either by itself or pre-loaded within the sheath 12. The obstruction removal device 8 is then advanced to the obstruction. Before advancing the obstruction removal device 8 further, the flow restricting element 6 on the guide catheter 4 is expanded to reduce and even stop flow through the vessel. Stopping flow in the vessel may help prevent the obstruction, or any parts thereof, from migrating downstream. Reducing flow through the vessel may also reduce the likelihood that the obstruction is disrupted by a combination of flow and the obstruction removal device 8.

The obstruction removal device 8 is then placed into the obstruction and preferably through the obstruction. The engaging element 16 is then advanced out of the microcatheter 10 or sheath 12 to permit the distal portion 20 of the engaging element 16 to expand at a location beyond the obstruction. In this manner, the relatively closed distal portion 20 prevents the obstruction, or any part thereof, from migrating downstream. The proximal portion 22 is then advanced out of the sheath 12 or microcatheter 10 so that the smaller coils of the proximal portion 22 engage the obstruction as shown in FIG. 4.

Figure 5:
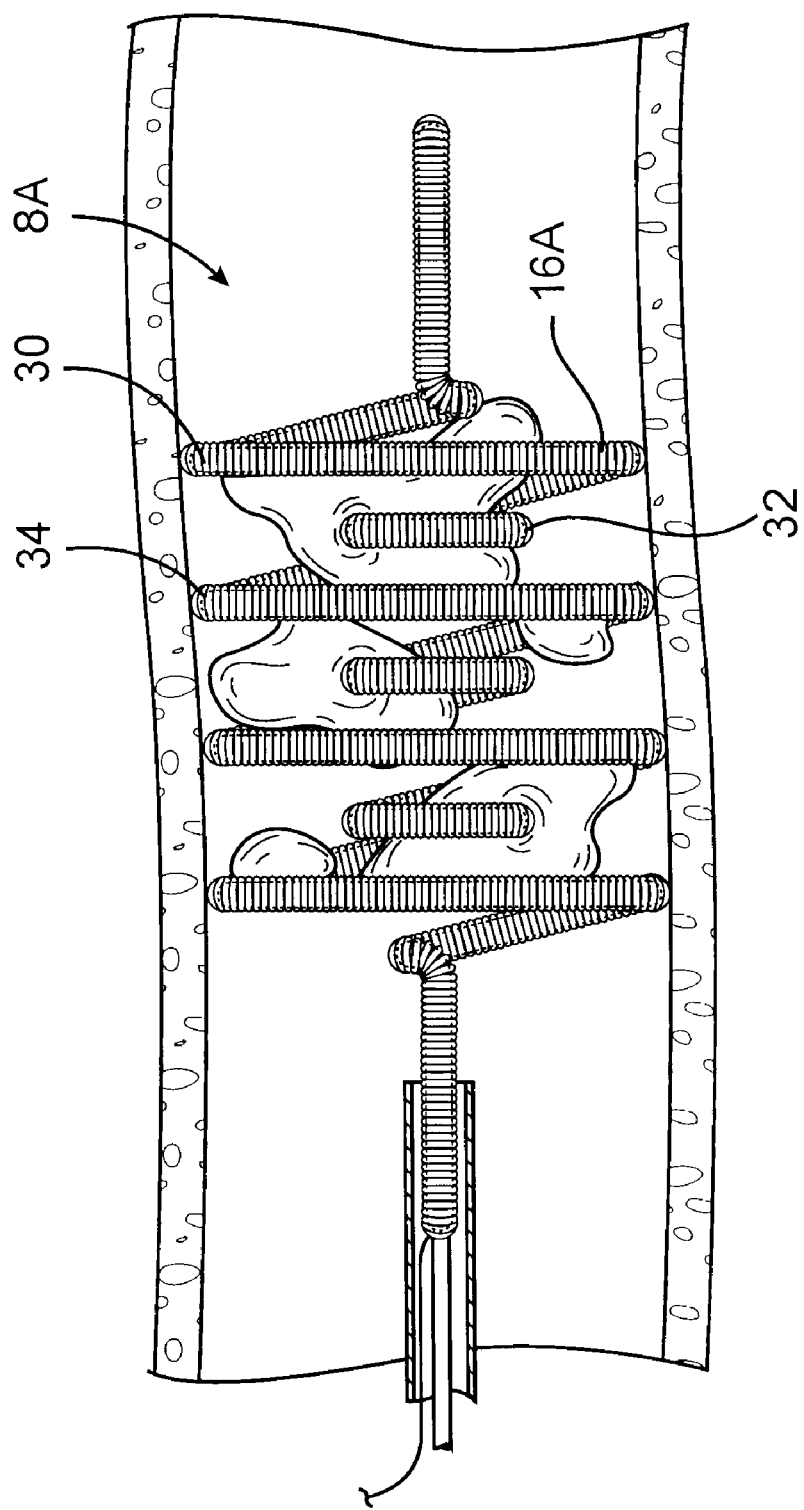
FIG. 5 shows another obstruction removal device.

Referring to FIG. 5, another obstruction removal device 8A is shown wherein the same or similar reference numbers refer to the same or similar structure. The obstruction removal device 8A has a first section 30 with larger diameter coils than a second section 32. A third section 34 also has larger coils than the second section 32 with the second section 32 positioned between the first and third sections 30, 34. The obstruction removal device 8A may have a number of alternating small and large sections 30, 32, 34 which can enhance the ability of the obstruction removal device 8A to engage various obstructions. In the preferred embodiment of FIG. 5, the obstruction removal device 8A has four large sections 32, 34 with relatively large coils and three sections 30 having smaller coils.

The obstruction removal device 8A may be used in any suitable manner to engage the obstruction. For example, the microcatheter 10 or sheath 12 may be advanced through the obstruction and then retracted to expose the obstruction removal device 8A. The obstruction removal device 8A is then retracted into the obstruction to engage the obstruction. The obstruction removal device 8A may be rotated when moved into the obstruction to take advantage of the generally helical shape of the obstruction removal device. The obstruction removal device 8A may also be used to engage the obstruction by simply retracting the microcatheter 10 or sheath 12 with the obstruction removal device 8A expanding within the obstruction. Finally, the engaging element 16A may be exposed and expanded proximal to the obstruction and then advanced into the obstruction. When advancing the obstruction removal device 8A into the obstruction, the user may also twist the obstruction removal device 8A to take advantage of the generally helical shape. The alternating large and small sections 30, 32, 34 enhance the ability of the engaging element 16A to engage varying shapes and sizes of obstructions.

Figure 6:
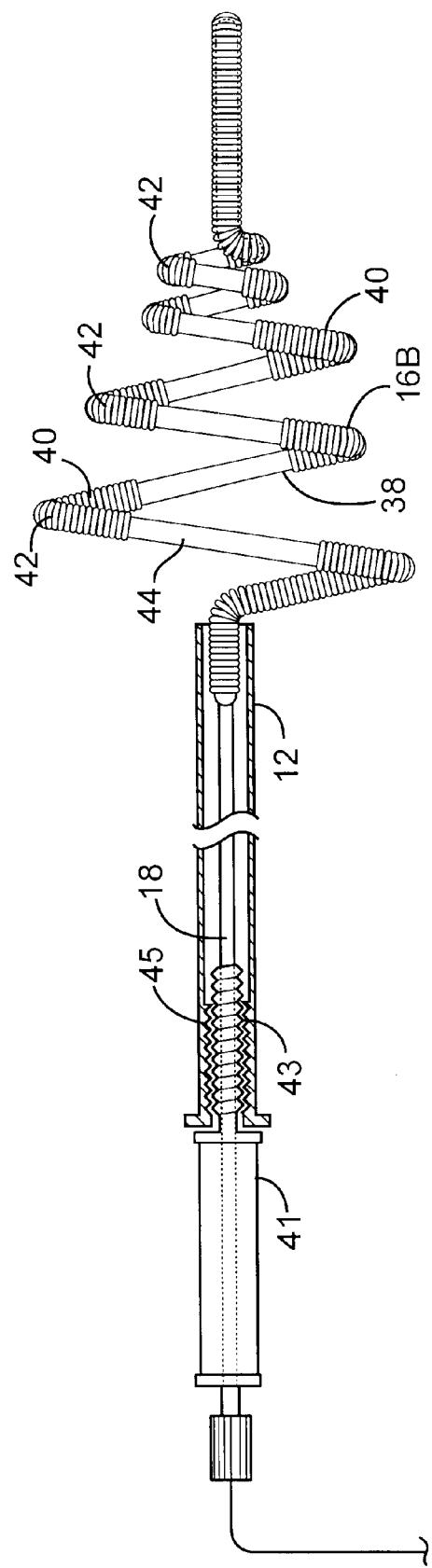
FIG. 6 shows yet another obstruction removal device.

Referring to FIG. 6, still another obstruction removal device 8B is shown wherein the same or similar reference numbers refer to the same or similar structure. The obstruction removal device 8B has the insertion element 18 with an engaging element 16B extending therefrom. The engaging element 16B forms a helical coil 38 with a generally frustoconical shape, however, the engaging element 16B may take any other shape without departing from the scope of the invention including any shape disclosed in this application or any patent incorporated by reference herein.

A filament 40, preferably a radiopaque filament, is wrapped around the engaging element 16B. The filament 40 is wrapped somewhat loosely around the engaging element 16B so that the filament 40 provides additional surface area to engage the obstruction. The filament 40 forms a wound section 42, and more preferably at least five wound sections 42, which are separated by substantially exposed sections 44 of the engaging element 16B. The wound and exposed sections 42, 44 may be 1–5 mm long. Stated another way, the wound and exposed sections 42, 44 are at least 1 mm, more preferably at least 3 mm long, and no more than 8 mm long. The wound sections 42 may be formed by a single filament 40 which extends continuously between the wound sections 42 or may be formed by independent filaments 40 at each wound section 42 which are attached to the engaging element 16B.

The wound sections 40 may be movable along the engaging element 16B to provide flexibility when advancing the obstruction removal device 8B through small and tortuous vessels. The movable wound sections 40 may also allow different parts of the obstruction removal device 8B to grip different parts of the obstruction to hold the obstruction together or engage different parts of the obstruction. The obstruction removal device 8B is used in substantially the same manner as the other obstruction removal devices described herein. The obstruction removal device 8B has a handle 41 with a lead screw 43 which engages threads 55. The handle 41 is rotated to advance and retract the engaging element 16B.

Figure 7:
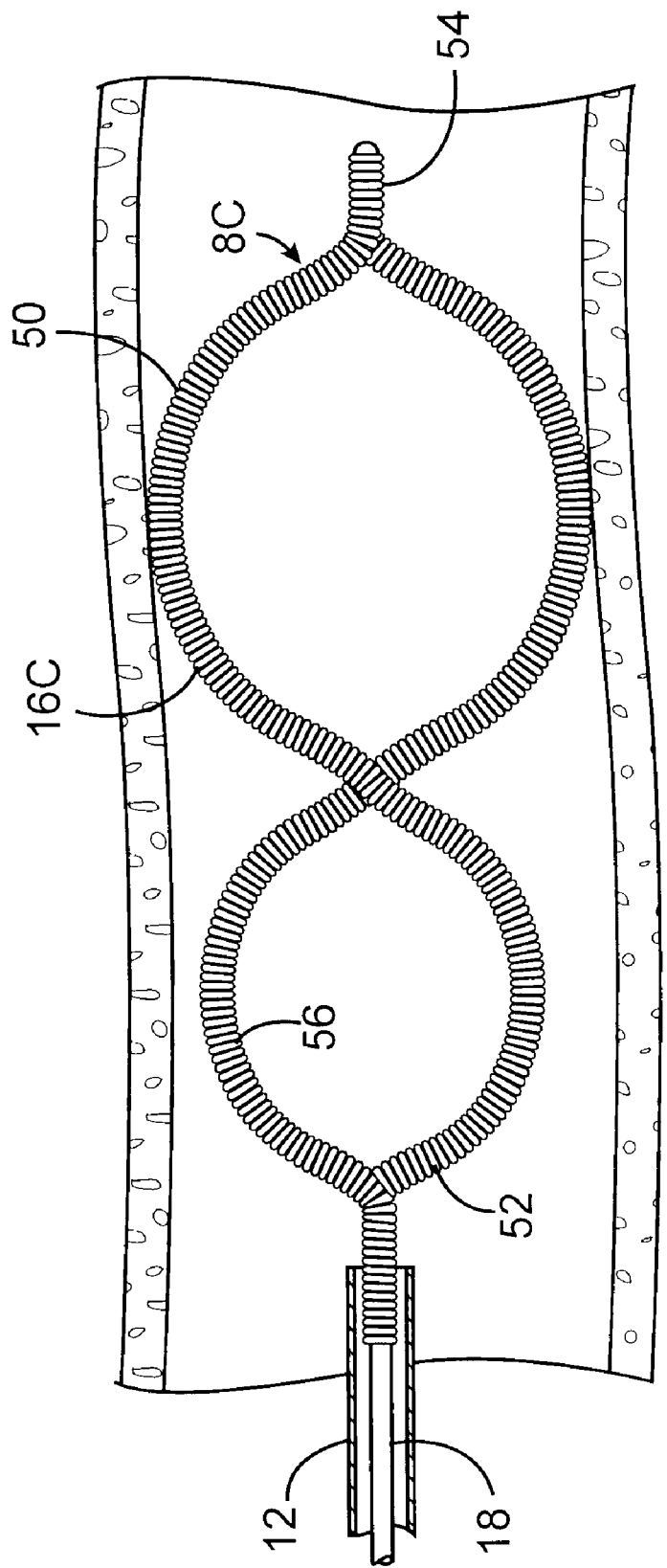
FIG. 7 shows still another obstruction removal device.

Referring to FIG. 7, still another obstruction removal device 8C is shown wherein the same or similar reference numbers refer to the same or similar structure. The obstruction removal device 8C has an engaging element 16C, which forms a first closed loop 50, and a second closed loop 52. The first loop 50 is preferably somewhat larger than the second closed loop 52 with the first loop 50 having a diameter of about 1.5–8.0 mm and the second loop 52 having a diameter of about 1.5–6.0 mm. A tip 54 extends from the first loop 50 for a distance of about 5 mm. A radiopaque element 56, such as platinum ribbon, is preferably wrapped around the loops 50, 52 to improve radiopacity and to enhance the ability of the engaging element 16C to hold the obstruction. The radiopaque element 56 also may provide advantages when engaging an obstruction in a manner similar to the obstruction removal devices described above with reference to FIG. 6.

Figure 8:
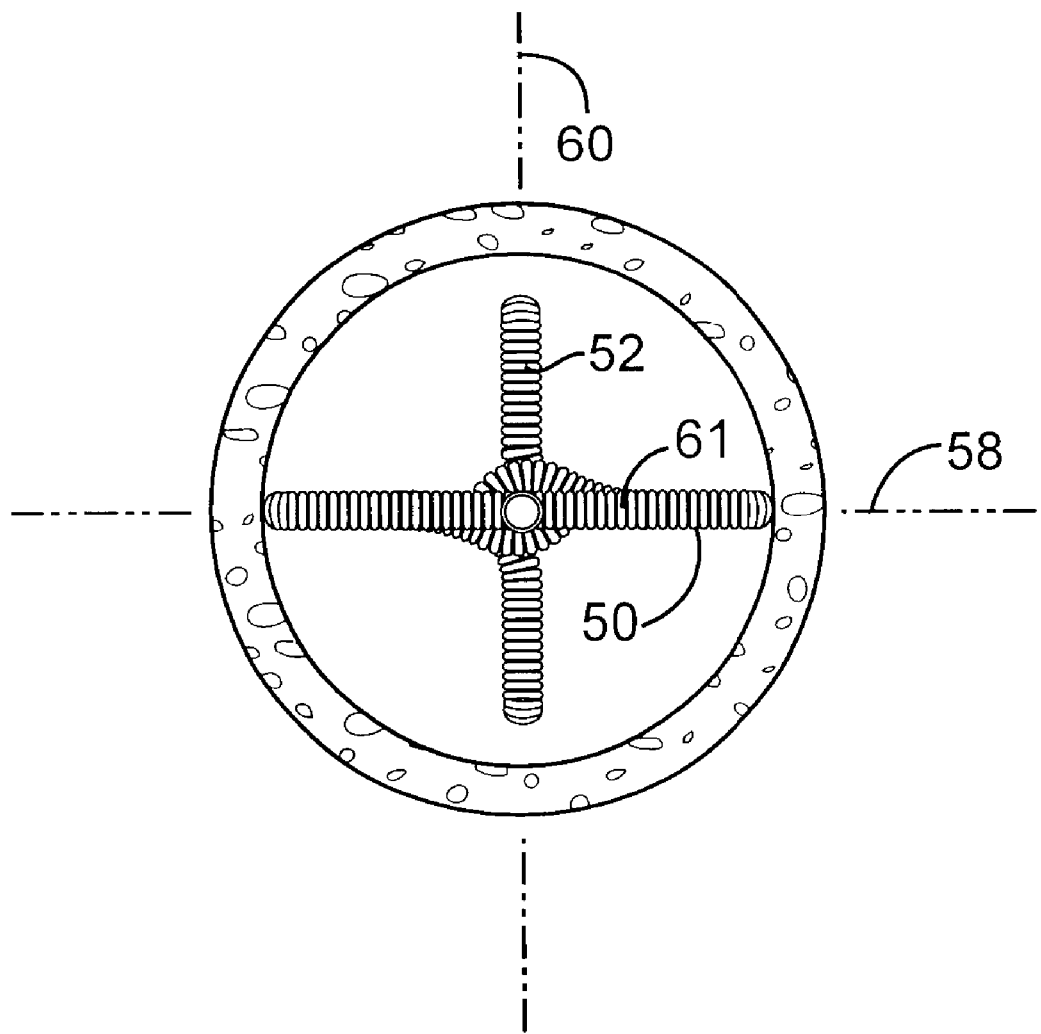
FIG. 8 is an end view of the obstruction removal device of FIG. 7.

An advantage of the obstruction removal device 8C is that the loops 50, 52 exert substantially equal and opposing forces on the sheath 12 or microcatheter 10 through which the obstruction removal device 8C is advanced. In this manner, kinking or binding of the obstruction removal device 8C during advancement can be minimized or reduced altogether. Referring to the end view of FIG. 8, the first and second loops 50, 52 preferably lie in first and second planes 58, 60, respectively, which are preferably perpendicular to one another.

Figure 9:
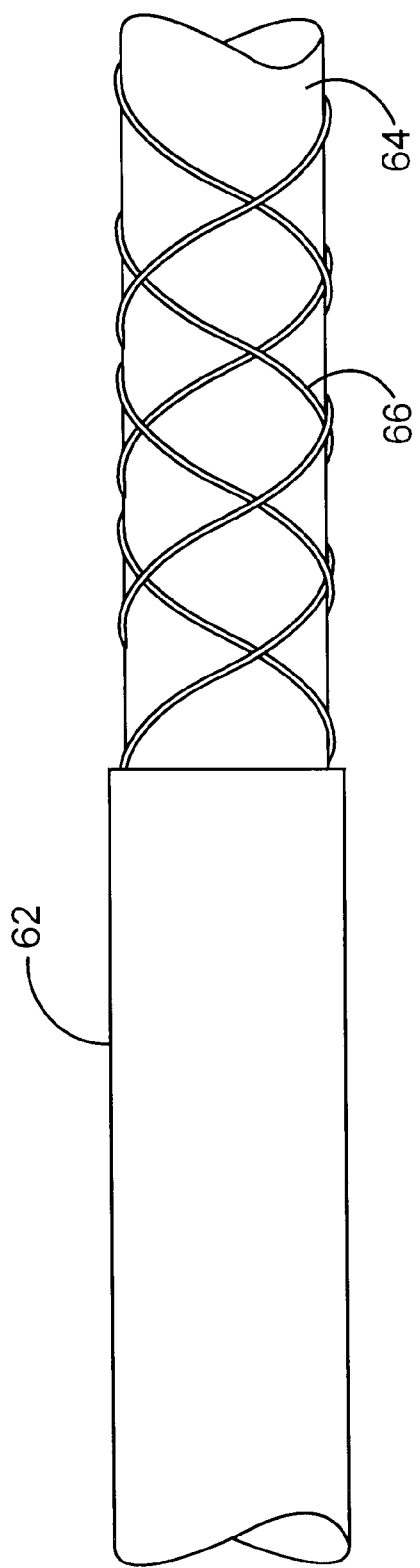
FIG. 9 is an exploded view showing a method of constructing an obstruction removal device.

Referring to FIG. 9, an exploded view of a construction of the obstruction removal device 8, 8A, 8B, 8C is shown. A tube 62, which is preferably a thermoplastic polymer such as polyester or urethane is positioned over a core element 64. As mentioned above, the core element 64 is preferably a superelastic or stainless steel element at either the insertion element 18 or the engaging element 16 (FIGS. 2–7). A reinforcing strand 66 is trapped between the tube 62 and the core element 64 to reinforce the obstruction removal device. The strand 66 is preferably small and has a diameter or thickness of less than 0.005 inch, more preferably less than 0.0001 inch, so that the overall size of the obstruction removal device is not increased significantly with use of the strand 66. The strand 66 may be made of any suitable material including VECTRAN made by Celanese Acetate LLP or DACRON or KEVLAR which are both manufactured by Dupont. VECTRAN is a thermoplastic multifilament yarn spun from a liquid crystal polymer.

The strand 66 provides a degree of safety in that the strand 66 and tube 62 together prevent any part of the obstruction removal device from breaking free from the rest of the device. The tube 62 will resist breaking since it is more flexible than the core element 64 and can undergo larger deflections and displacements without breaking. In a preferred embodiment, 2–8 strands 66, preferably about 4 strands 66, are used. The overall size of the device is also relatively small with the outer diameter of the resulting structure being no more than 0.020 inch and more preferably no more than 0.012 inch.

The power source 14 may be also be used with any of the obstruction removal devices in the following manner, however, the methods and devices of the present invention may, of course, be practiced without the power source 14. As mentioned above, the power source 14 may simply produce a charge at the engaging element 16 or may be a source of RF energy. In one particular method of the present invention, the power source 14 produces a negative charge while advancing the engaging element 16 through the obstruction. The negative charge may aid in passing the engaging element 16 through the obstruction and may help to dissolve part of the obstruction. The power supply is then changed to produce a positive charge to adhere the obstruction to the engaging element 16. Alternatively, the power source 14 may be an RF energy source, which delivers RF to the engaging element 16 which also adheres the obstruction to the engaging element 16 and may help provide a controlled penetration into the obstruction. The obstruction is then removed by moving the obstruction into the guide catheter 4, which is then withdrawn to remove the obstruction. Use of the power source 14 is particularly useful when the obstruction is a biologic structure such as a clot.

Referring to FIGS. 10–14, another system 100 for removing an obstruction is shown. The system 100 is particularly useful for removing clots and thrombus from blood vessels but may also be used to remove other obstructions such as embolic coils and the like. The system 100 includes an expandable capture element 102 and an obstruction engaging device 106 which work together to capture the obstruction. The obstruction engaging device 106 engages the obstruction and moves the obstruction into the capture element 102 as described below. After the obstruction has been captured, the capture element 102 may then be used in various ways for ultimate removal of the obstruction. The capture element 102 may be advanced through the guide catheter 4 or through another catheter 107 which is advanced through the guide catheter 4. As will be explained below, the capture element 102 is preferably advanced over the obstruction engaging device 106.

The obstruction engaging device 106 may be any of the engaging or removal devices described herein or any other suitable device. Various aspects of the invention preferably include one or more features of the obstruction removing devices described herein and all aspects, features, dimensions, and characteristics of the obstruction removing and engaging devices described herein are incorporated here. It is understood that the term obstruction removal device and obstruction engaging device are interchangeable. The obstruction engaging device 106 may be contained within the sheath 12 or may be advanced by itself through the guide catheter 4 and/or catheter 107.

The engaging device 106 may have one or more filaments 108, preferably 1–4 and more preferably 1–2 filaments, which engage the obstruction. The filament 108 forms a relatively small, flexible interaction between the engaging device 106, capture element 102 and obstruction which provides advantages over the prior art method of using a balloon catheter. The filament 108 may deflect and displace to accommodate the geometry and orientation of the obstruction when the obstruction enters the capture element 102. The interaction between the balloon catheter and the expandable catheter of the prior art tends to shear off portions of the obstruction due to the relatively rigid interaction between the balloon catheter and expanded catheter. The filament 108 also has a relatively small size which further enhances the flexibility of the obstruction engaging device 108. The filament 108 may also form one or more loops 110 which further serve to create a soft, flexible interaction between the obstruction engaging device 106 and capture element 102. The filaments 108 may also form a filter which further prevents the obstruction or portions thereof from travelling downstream.

The capture element 102 preferably has a support structure 112 with a flexible cover 114 attached thereto. The support structure 112 is preferably self-expanding although the support structure 112 may also be selectively expanded by the user as explained below. The support structure 112 preferably has a loop 116 having integrally formed hinges 117. The hinges 117 are preferably formed by V-shaped interconnecting elements 120 although other shapes, such as U-shaped, may be used. The loop 116 is preferably formed as an integral structure with the loop 116 being formed from a tube of material which is cut, etched, treated or otherwise formed into the loop 116 with hinges 117. The loop is preferably made of a superelastic material although any suitable material may be used.

Figure 14:
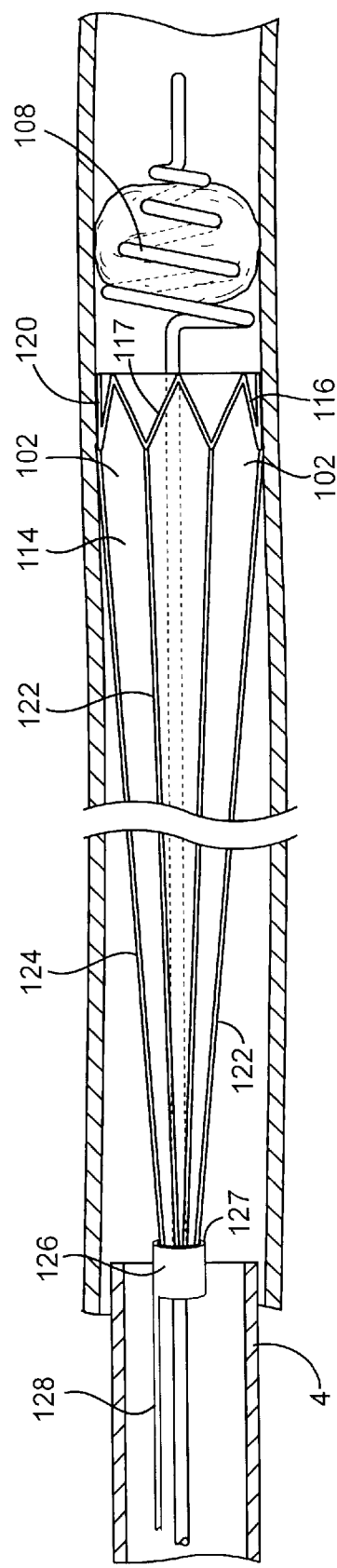
FIG. 14 shows an alternative structure for the capture element.
Figure 15:
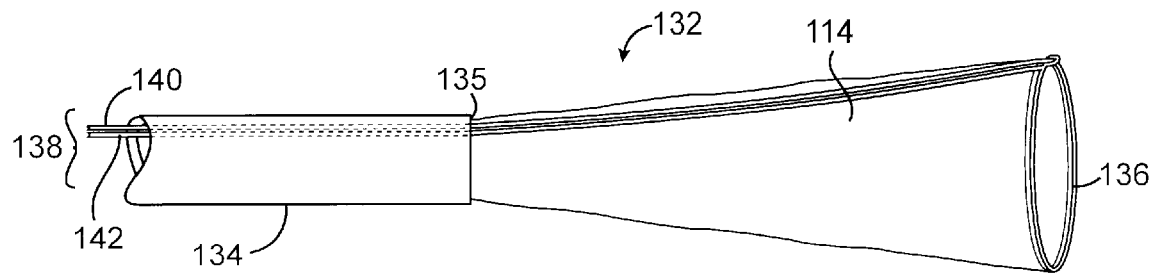
FIG. 15 shows another capture element.
Figure 16:
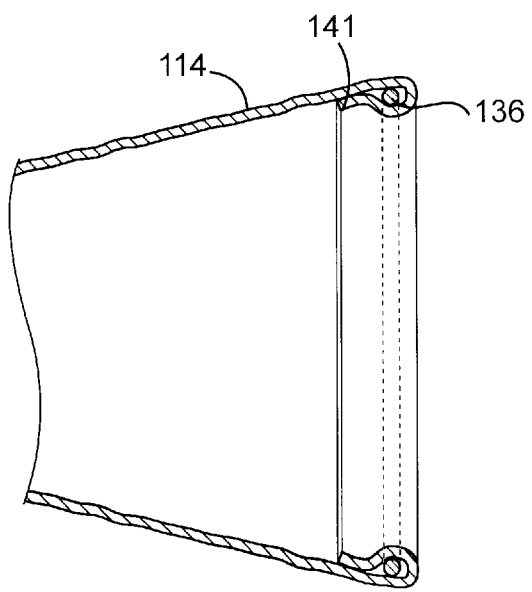
FIG. 16 shows a distal end of the capture element of FIG. 15.
Figure 17:
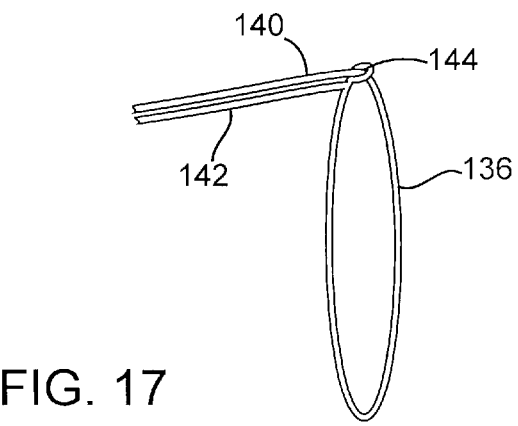
FIG. 17 shows the support structure for the capture element of FIGS. 15 and 16.
Figure 23:
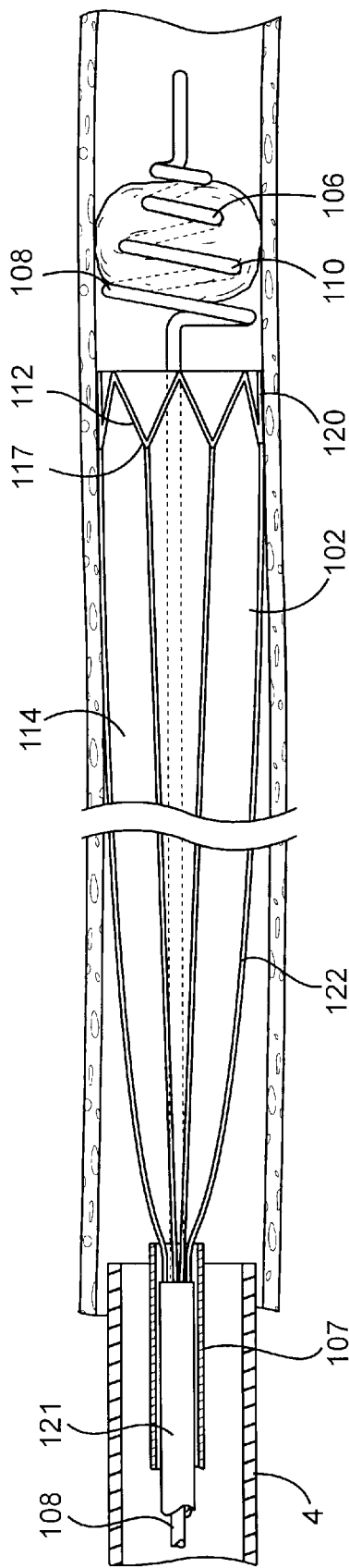
FIG. 23 shows another capture element having a support structure which bows outward to preferentially close the distal end.
Figure 24:
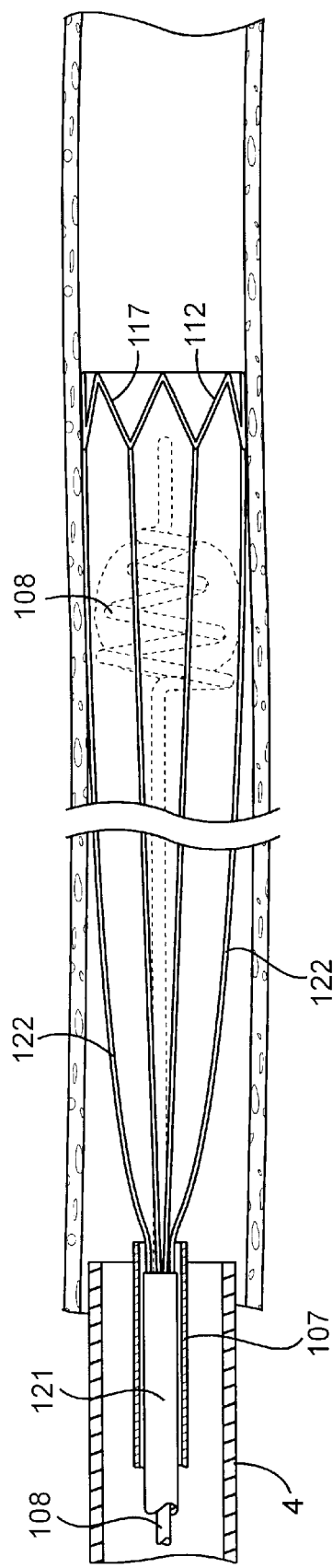
FIG. 24 shows the capture element of FIG. 23 with an obstruction contained within the capture element.

Struts 122 extend proximally from the loop 116. The struts 122 do not intersect and generally form a cone 124 when expanded. The struts 122 are coupled to a lumen 121 which receives the engaging device 106 so that the capture element 102 can be advanced over the engaging device 106 as described below. Referring also to FIG. 14, the struts 122 may also be coupled together at a hub 126 at the proximal end. The hub 126 has a lumen 127 which receives the engaging device 106. A shaft 128 extends from the hub 126 and is used to manipulate the capture element 102. The struts 122 are preferably made of a superelastic material or stainless steel and are attached to the closed loop 116 by soldering, welding, glue or any other suitable attachment method. The struts 122 may also be integrally formed with the loop 116. Of course, the supporting structure 112 may be made of any other suitable material and may be formed in any other suitable manner. The struts 122 may also be bowed outward so that the distal end of the device is preferentially closed before the entire device has been withdrawn as shown in FIGS. 23 and 24.

The cover 114 is preferably attached to the support structure 112 with glue, thread, suture or any other suitable method. The cover 114 preferably lies over the support structure 112 but may also be contained within the support structure 112. The cover 114 is relatively long to ensure that the entire obstruction is captured. The cover 114 is preferably at least three times, more preferably at least five times, and most preferably at least seven times larger than the maximum expanded diameter of the support structure 112 or cover 114. Of course, the capture element 102 may have any other suitable dimensions depending upon the particular application. The cover 114 is preferably made of ePTFE but may be made of any other suitable material. The cover 114 may also be a mesh-like structure, or any other suitable expandable structure which can contain the obstruction and parts thereof, without departing from the scope of the invention.

Various methods of the present invention are now described. The methods are described in connection with system 100 of FIGS. 10–14 but may be practiced with other suitable devices and systems. The present invention is well-suited for use in the cerebral vasculature and a cerebral application is described, however, the invention may be practiced in other vascular locations as well.

The guide catheter 4 is advanced to a suitable location. The obstruction engaging device 106 is then advanced through the guide catheter 4. Referring to FIGS. 11 and 12, the obstruction engaging device 106 is then used to engage the obstruction in any manner described herein. For example, the sheath 10 (see FIG. 10) may be advanced through the obstruction and then retracted so that a proximal portion 111 of the device 106 is contained within the obstruction. The device 106 is then moved proximally, and is preferably twisted, so that the loops 110 engage the obstruction. In the specific embodiment of FIGS. 11–14, the device 106 ensnares the obstruction with the loops 110 when twisted and moved proximally.

Figure 13:
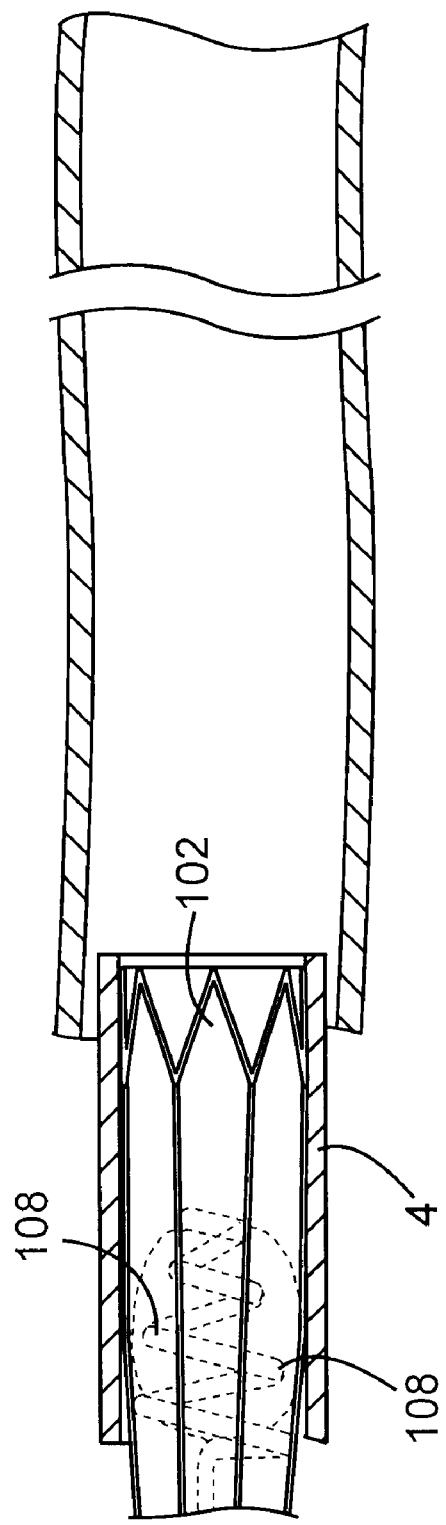
FIG. 13 shows the capture element collapsed and contained within a catheter.

The capture element 102 is then advanced over the engaging device 106. The capture element 102 may be advanced through the guide catheter 4 or may be advanced through the catheter 107 which is advanced through the guide catheter 4 further into the cerebral vasculature. The capture element 102 is then moved out the catheter 107 or guide catheter 4 so that the capture element 102 expands. The obstruction is then moved into the capture element 102 with the device 106 as shown in FIG. 13. When the obstruction is contained within the capture element 102, the capture element 102 is then withdrawn into the catheter 107 or guide catheter 4 as shown in FIG. 14. The catheter 107 and/or guide catheter 4 are then withdrawn from the patient thereby withdrawing the obstruction.

Figure 22:
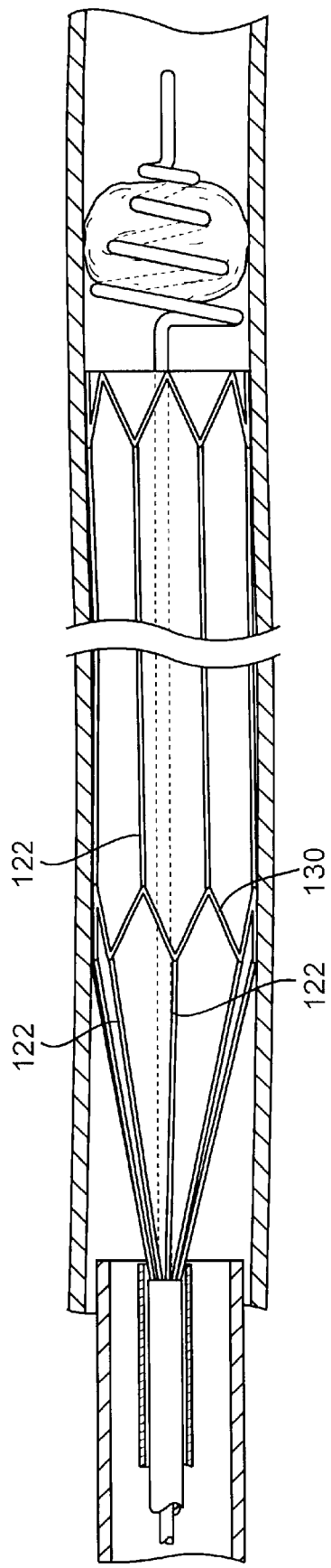
FIG. 22 shows still another support structure for the capture element.

It may be desirable to reduce or even stop blood flow through the blood vessel during the procedure to reduce flow forces on the obstruction when manipulating the obstruction. Reducing flow in the vessel may also prevent some parts of the obstruction from breaking off and flowing downstream before entering the capture element 102. Referring again to FIGS. 10 and 22, blood flow may be reduced by inflating a balloon 131 on the guide catheter 4 or the catheter 107. The balloon 131 is inflated using a suitable source of inflation fluid 133. Alternatively, the capture element 102 itself may also be used to reduce blood flow through the vessel. The capture element 102 naturally impedes blood flow since it expands within the blood vessel. The capture element 102 may also be designed to only partially occlude the vessel so that some blood flow is provided to the area downstream from the capture element 102. The device 102 may be modified to include a second loop 130 extending between the struts 122 to enhance the ability of the device 102 to occlude the vessel. The loop 130 preferably has the features of the loop 116. Although it is preferred to reduce or even stop flow in the vessel, the invention may also be practiced without reducing blood flow.

The devices and methods of the present invention may also be practiced with a source of vacuum 135 providing suction during capture of the obstruction. The source of vacuum 135 may be activated during engagement of the obstruction with the device 106, movement of the obstruction into the capture element 102, and/or withdrawal of the capture element 102 into the catheter 107 or guide catheter 4. The source of vacuum 135 is coupled to the guide catheter, 4, catheter 107 and lumen 121 for these purposes.

Referring to FIGS. 10 and 15–17, another capture element 132 for removing an obstruction is shown wherein the same or similar reference numbers refer to the same or similar structure. The capture element 132 is selectively expandable by the user which provides various advantages described below. The cover 114 is attached to a catheter 134 near or at the distal end 135. The catheter 134 may be the guide catheter 4 or the catheter 107 in the system 100 described above. An expandable and collapsible loop 136 is attached to the distal end of the cover 114 to expand and collapse the distal end of the cover 114. The loop 136 is expanded and collapsed by manipulating an actuator 138 which includes a control arm 140 and a stable arm 142. The control arm 140 extends and slides through an eyelet 144 when expanding and collapsing the loop 136. The stable arm 142 extends from the loop 136 at or near the eyelet 144 to stabilize the loop 136 when moving the control arm 140. The cover 114 is attached to the loop 136 using any suitable method. For example, the distal end may be inverted to create a fold 141 which surrounds the loop 136.

Another advantage of the capture element 132 is that the capture element 132 may be selectively expanded and contracted by the user. The capture element 132 may be fully or partially collapsed to trap the obstruction prior to withdrawal of the capture element 132 into the catheter 107 or guide catheter 4 as shown in FIG. 18. In fact, the capture element 132 may be withdrawn by itself by simply closing the distal end and withdrawing the capture element 132. In this manner, the capture element 132 protects the obstruction during withdrawal and prevents the obstruction from escaping. This provides obvious advantages over the system of Guenther described above.

Figure 10:
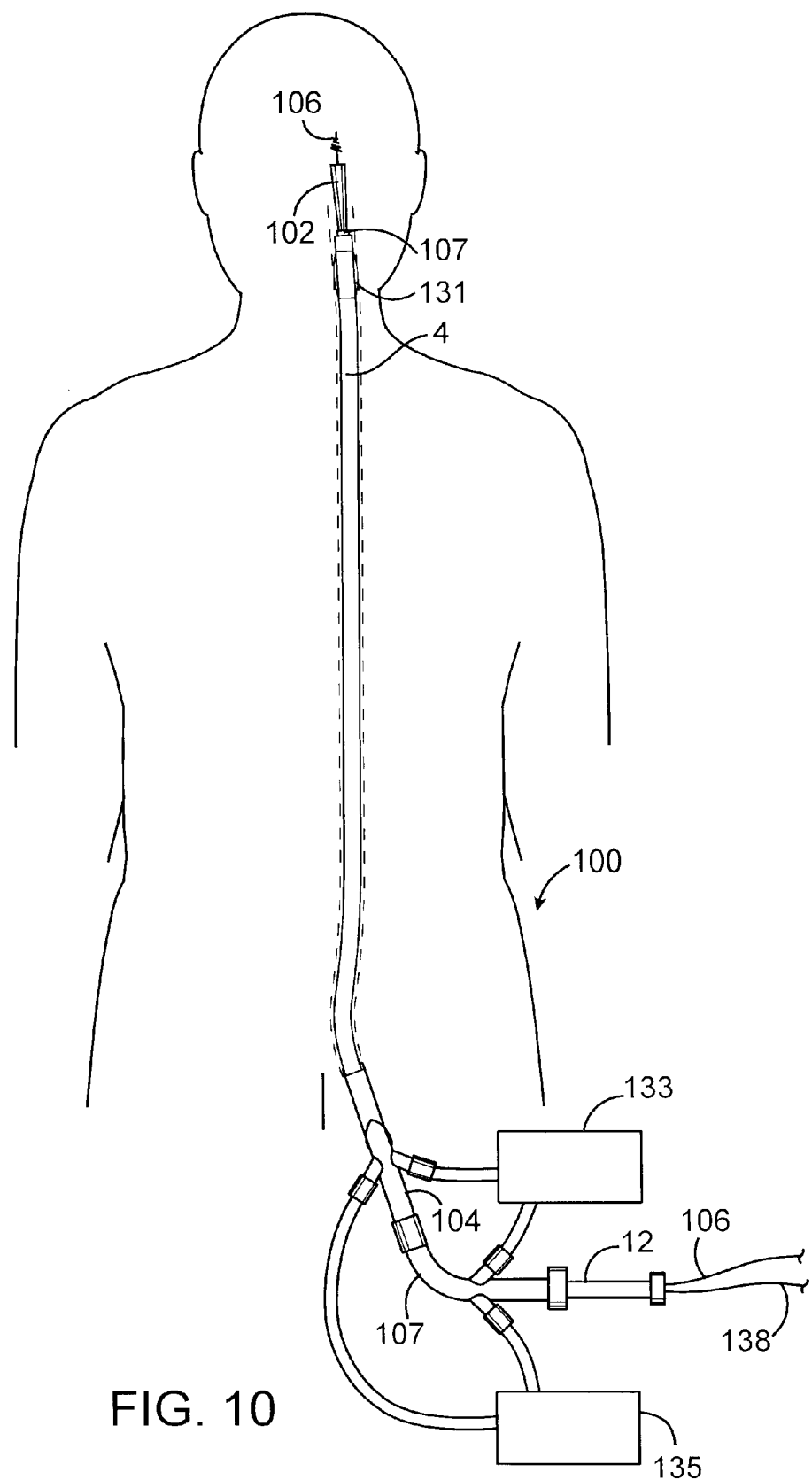
FIG. 10 shows another system for removing an obstruction from a blood vessel.

Referring to FIGS. 10 and 19, still another capture element 150 is shown in which the same or similar reference numbers refer to the same or similar structure. The capture element 150 has the cover 114 and the actuator 138 which includes the stable arm 142, control arm 140, and loop 136 although other actuating structures may be used. The capture element 150 is contained within the catheter 107 or the guide catheter 4 during introduction and is then everted out of the catheter 107 or catheter 4 when deployed. The capture element 150 may be used in substantially the same manner as the other capture elements described herein and in particular the capture element 132 of FIGS. 15–17. The capture element 150 may also be used to further collapse the cover 114 since the actuator 138 may be used to close the distal end with the cover 114 deployed. After the obstruction is contained within the capture element 150, the capture element 150 is withdrawn into the catheter 107 or catheter 4. Although it is preferred to withdraw the capture element 150 into the catheter 4 or catheter 107, the capture element 150 may be collapsed and then inverted back into the catheter 4, 107 thereby trapping the obstruction in the catheter 4, 107 itself.

Figure 20:
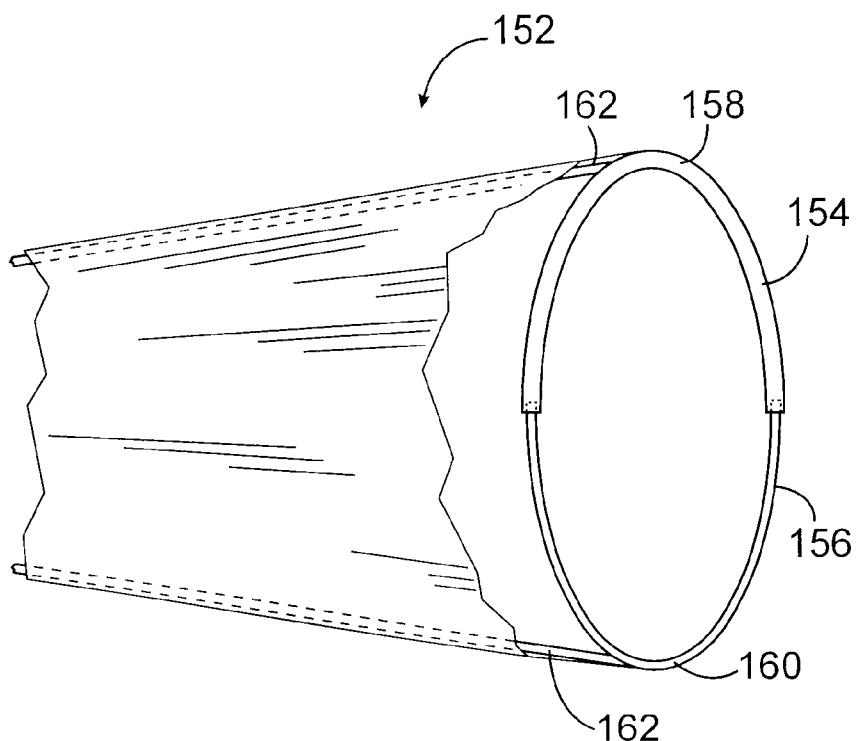
FIG. 20 shows another support structure for the capture element with the support structure in an expanded position.
Figure 21:
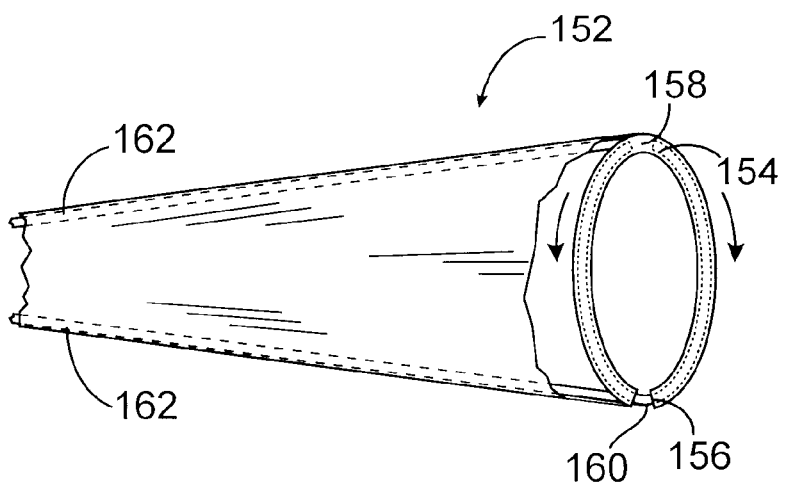
FIG. 21 shows the support structure of FIG. 20 in a collapsed position.

Referring to FIGS. 20 and 21, the distal end of yet another capture element 152 is shown in which the same or similar reference numbers refer to the same or similar structure. The capture element 152 has a self-expanding support structure 154 with an expandable loop 156 at the distal end. The loop 156 has a tube 158 which receives a wire 160 at both ends. The slidable connection between the tube 158 and wire 160 permits the loop 156 to contract and expand between the positions of FIGS. 20 and 21. Struts 162 extend from the loop which engage the catheter to collapse the loop 156. The cover 114 is attached to the loop 156 by any suitable method. The capture element 152 is used in any manner described herein. The capture element 152 is used in any manner described herein and those methods are incorporated here.

Figure 25:
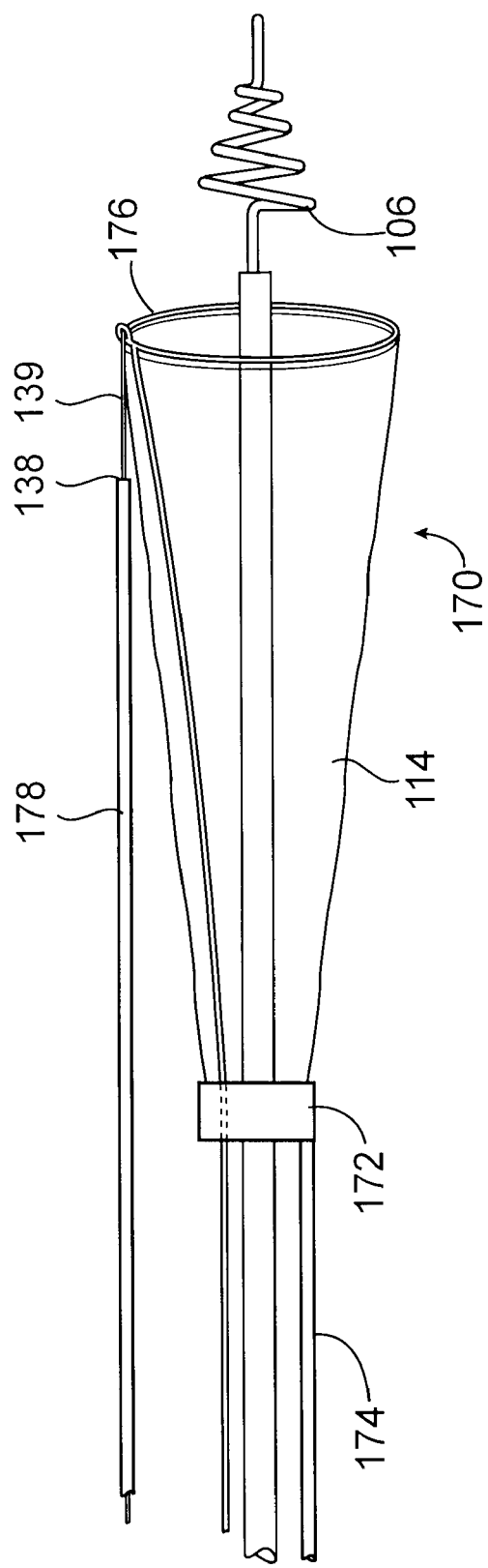
FIG. 25 shows another capture element.

Referring to FIG. 25, still another device 170 is shown wherein the same or similar reference numbers refer to the same or similar structure. The device 170 is similar to the device of FIG. 15 in that the device 170 may be selectively expanded and collapsed by the user. The device 170 has a collar 172, which may also be a continuous sheath or tube, which slides over the catheter 107 or sheath 12. The engaging device 106 passes through the catheter 107 or sheath 12 (FIG. 10) and is used in the manner described herein. A 174 wire, or other elongate member, is coupled to the collar 172 for advancing and manipulating the collar 172.

The cover 114 is coupled to a loop 176 which is selectively expanded by the user as now explained. The loop 176 is manipulated with the actuator 138 which may be any suitable mechanism. The actuator 138 has a wire 139 passing through an actuator tube 178 and may also include the stable arm 142. The wire 139 is coupled to the loop so that movement of the wire 139 opens and closes the loop 176. The actuator tube 178 may be simply advanced to cinch the loop 176 closed. The loop 176 is preferably naturally biased toward the open position and is held closed by the tube 178.

The device 170 is used in substantially the same manner as the other devices described herein and discussion of those methods are specifically incorporated here. The device 170 may be advanced by itself through the vasculature with the tube 178 holding the loop 176 in the closed position. The cover 114 is advanced by manipulating the tube 178, wire 139 and wire 174. The cover 114 is advanced over the catheter 107 or sheath 12 and the tube 178 is retracted to permit the loop 176 to expand. The obstruction is then introduced into the cover 114 and the cover 114 is then closed by advancing the tube 178 to cinch the loop 176 closed. The actuator 138 may also be manipulated to open or close the loop 176 together with the tube 178 or independently of the tube 178.

Figure 26:
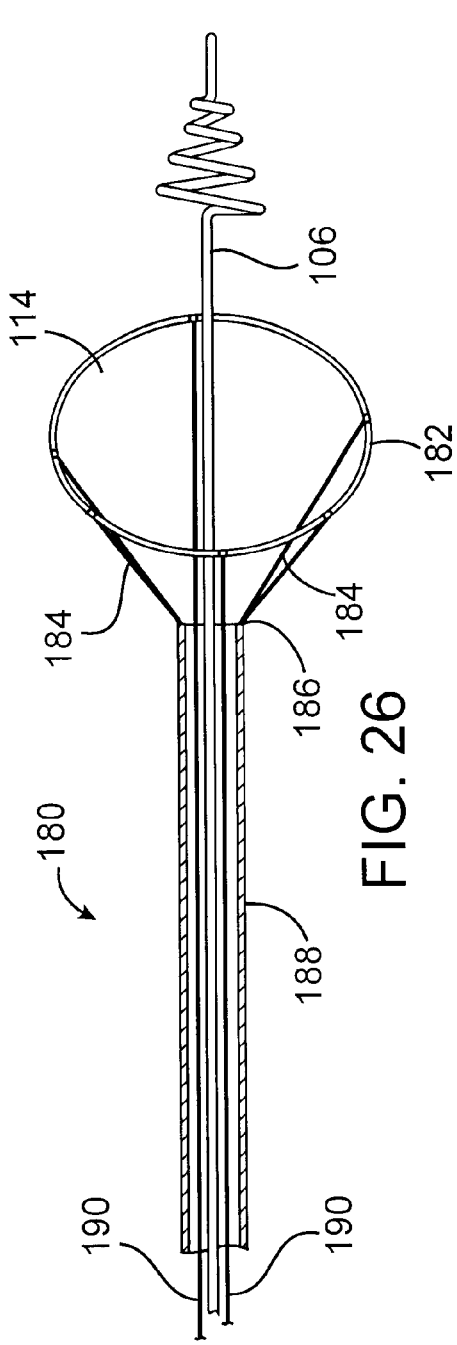
FIG. 26 shows yet another capture element in an expanded position.
Figure 27:
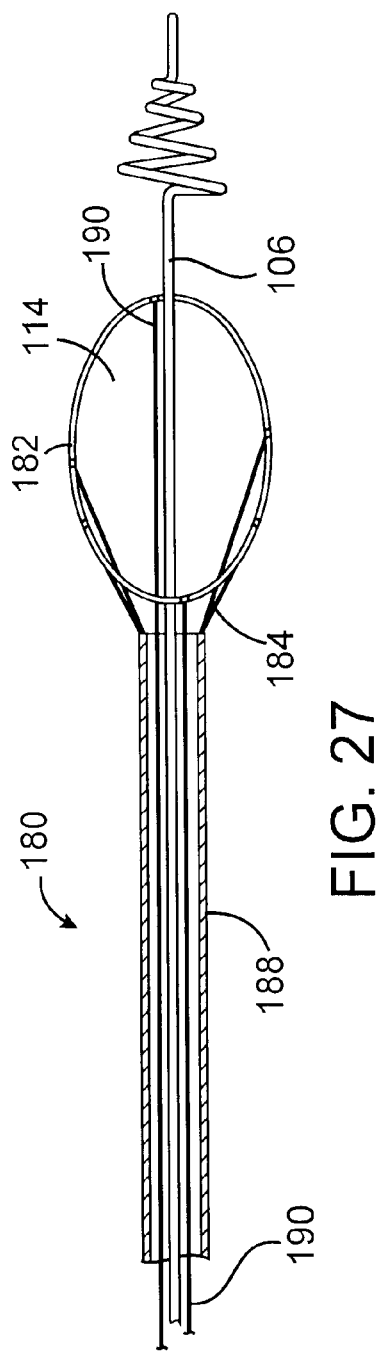
FIG. 27 shows the capture element of FIG. 26 in a collapsed position.

Referring to FIGS. 26 and 27, still another device 180 is shown wherein the same or similar reference numbers refer to the same or similar structure. The device 180 has the cover 114 and a loop 182 coupled to the distal end of the cover 114. Stabilizing struts 184 extend from an end 186 of a tubular body 188 to the loop 182. Actuating arms 190 extend through the body 188 and are also attached to the loop 182. The arms 190 are manipulated to move the loop 182 between the collapsed and expanded positions of FIGS. 26 and 27. The engaging device 106 passes through the body 188 and may be delivered through the catheter 107 or sheath 12. The device 180 is used in substantially the same manner as the device of FIG. 15 and discussion of those methods are incorporated here.

While the above is a description of the preferred embodiments of the invention, various alternatives, substitutions and modifications may be made without departing from the scope thereof, which is defined by the following claims. Thus, the preferred embodiments should not be taken as limiting the scope of the invention. For example, although all of the obstruction removal devices described herein are self-expanding structures, the obstruction removal devices may also have actuating mechanisms for moving the engaging element between the expanded and collapsed positions. Furthermore, the present invention is directed to a number of separate inventions and each of these inventions may be claimed independently of one another. Each feature, aspect and advantage of the invention may be claimed independent of one another without departing from the scope of the invention. For example, use of the power source 14 is independent of the using the intermittent wound sections 42 but may be used with any of the devices and methods described herein. As a further example, any engaging device, even a balloon, may be used with some of the inventive aspects of the capture element and any capture element may be used with inventive aspects of the engaging device. Finally, the devices of the present invention may also be used in connection with simply controlling blood flow through an area and not necessarily with removal of an obstruction. Thus, it is understood that various aspects of the present invention are not limited to removal of obstructions. Thus, the invention does not include a single essential feature, aspect or advantage and the invention should not be limited as such. Finally, the preferred dimensions, materials and methods of manufacture described for any of the embodiments is equally applicable for other embodiments.

What is claimed is:

1. A system for removing an obstruction from a blood vessel, comprising:

a catheter having a lumen;

an expandable capture element which is contained within the lumen of the catheter, the capture element being slidable within the lumen of the catheter between a collapsed position contained within the lumen and an expanded position in which the capture element is positioned outside the lumen, the expandable capture element having a support structure with a flexible cover attached to the support structure, the self-expanding support structure having a closed loop with integrally formed hinges; and an obstruction engaging device having a filament, the filament being movable from a collapsed position to an expanded position, the obstruction engaging element passing through the catheter.

2. The system of claim 1, wherein:

the expandable capture element is naturally biased toward the expanded position when positioned outside the lumen.

3. The system of claim 1, wherein:

the hinges are V-shaped interconnecting elements.

4. The system of claim 1, wherein:

the support structure has a plurality of longitudinal struts extending from the loop.

5. The system of claim 1, wherein:

the capture element has an expandable loop at the distal end.

6. The system of claim 1, wherein:

the cover has a length which is at least three times an expanded diameter of the capture element.

7. The system of claim 6, wherein:

the length of the cover is at least five times the expanded diameter of the capture element.

8. The system of claim 1, wherein:

the engaging device has 1–4 filaments.

9. A method of removing an obstruction from a blood vessel comprising the steps of:

providing a catheter, an obstruction engaging device and an expandable capture element, the capture element being contained within a lumen of the catheter in a collapsed position, the capture element moving to an expanded position when positioned outside the lumen, the obstruction engaging device having a filament which is movable from a collapsed position to an expanded position;

introducing the catheter into a blood vessel of a patient;

engaging an obstruction with the filament, the filament penetrating and ensnaring the obstruction;

expanding the capture element; and moving the obstruction into the capture element with the engaging device after the engaging and expanding steps.

10. The method of claim 9, wherein:

the expanding step is carried out with the capture element being naturally biased toward the expanded position with a self-expanding support structure.

11. The method of claim 10, wherein:

the providing step is carried out with a flexible material attached to the support structure.

12. The method of claim 11, wherein:

the providing step is carried out with the self-expanding support structure having a closed loop.

13. The method of claim 11, wherein:

the providing step is carried out with the loop being integrally formed.

14. The method of claim 11, wherein:

the providing step is carried out with the support structure has a plurality of longitudinal struts.

15. The method of claim 14, wherein:

the providing step is carried out with the support structure having a loop being formed by a number of integrally formed hinges.

16. The method of claim 15, wherein:

the providing step is carried out with the hinges being V-shaped elements.

17. A system for removing an obstruction from a blood vessel, comprising:

a catheter having a lumen;

an expandable capture element contained within the lumen of the catheter, the capture element being in a collapsed position when contained within the lumen and being in an expanded position when positioned outside the lumen, the expandable capture element having a support structure forming a closed loop having a plurality of integrally formed hinges; and an obstruction engaging device which extends through the expandable capture element, the engaging device having a collapsed shape and an expanded shape.

18. A system for removing an obstruction from, a blood vessel, comprising:

a catheter having a lumen;

an expandable capture element which is contained within the lumen of the catheter, the capture element being slidable within the lumen of the catheter between a collapsed position contained within the lumen and an expanded position in which the capture element is positioned outside the lumen, the capture element having an expandable loop at the distal end, the loop being formed by an eyelet with a control arm extending through the eyelet; and an obstruction engaging device having a filament, the filament being movable from a collapsed position to an expanded position, the obstruction engaging element passing through the catheter.

19. The system of claim 18, wherein:

the expandable capture element has a support structure with a flexible cover attached to the support structure.

20. The system of claim 19, wherein:

the cover has a length which is at least three times an expanded diameter of the capture element.

21. The system of claim 20, wherein:

the length of the cover is at least five times the expanded diameter of the capture element.

22. The system of claim 18, wherein:

the engaging device has 1–4 filaments.

23. A method of removing an obstruction from a blood vessel comprising the steps of:

providing a catheter, an obstruction engaging device, a flexible material and an expandable capture element, the capture element being contained within a lumen of the catheter in a collapsed position, the capture element moving to an expanded position when positioned outside the lumen, the obstruction engaging device having a filament which is movable from a collapsed position to an expanded position, the flexible material being attached to a self-expanding support structure, the support structure forming a loop and having a plurality of longitudinal struts and being formed by a number of integrally formed hinges;

introducing the catheter into a blood vessel of a patient;

engaging an obstruction with the filament;

expanding the capture element, the capture element being naturally biased toward the expanded position with the self-expanding support structure; and moving the obstruction into the capture element with the engaging device after the engaging and expanding steps.

24. The system of claim 17, wherein:

the capture element has a flexible cover attached to the support structure, the cover having a distal end which is positioned at the loop so that the loop opens the distal end of the cover.

25. The system of claim 17, wherein:

the support structure has a plurality of longitudinal struts which extend proximally from the loop.

26. The system of claim 24, wherein:

the struts do not intersect and form a form a conical shape when the capture element is in the expanded.

27. The system of claim 17, wherein:

the loop has integrally formed hinges.

28. The system of claim 26, wherein:

the hinges are formed by V-shaped elements.

29. The system of claim 17, wherein:

the obstruction engaging device has a filament configured to penetrate and engage an obstruction.

* * * * *